United States Patent [19]

Roos et al.

[11] 3,987,363

[45] Oct. 19, 1976

[54] APPARATUS FOR TESTING THIN LAYERS OF BUBBLE DOMAIN MATERIAL FOR DEFECTS

[75] Inventors: Jan Roos; Jan Harm Tromp, both of Eindhoven, Netherlands

[73] Assignee: U.S. Philips Corporation, New York, N.Y.

[22] Filed: May 8, 1975

[21] Appl. No.: 575,605

[30] Foreign Application Priority Data

May 24, 1974 Netherlands ............... 7406964

[52] U.S. Cl. ..................... 324/34 R; 340/174 TC
[51] Int. Cl.² ............................................ G01R 33/12
[58] Field of Search ............ 324/34 R, 37, 43 R; 340/174 TC, 174 TF

[56] References Cited
UNITED STATES PATENTS 3,893,023  7/1975  Otala .............................. 324/43 R

OTHER PUBLICATIONS

Kurtzig et al., A New Direct Measurement etc., IEEE Trans. on Mag., vol. Mag-4, No. 3, Sept. 1968, pp. 426–430.
Shumate, Jr., Operational Method etc., Jour. of App. Phy. (JAP), vol. 42, Mar. 1–15, 1971, pp. 1274–1275.
Shumate, Jr., Magnetooptic–Measurement, IEEE Trans. on Magnetics (IEEE), Sept. 1971, pp. 586–590.
Argyle, Staining Defects, IBM Tech. Bull., vol. 15, No. 11, Apr. 1973, pp. 3582–3583.
Argyle et al., Dynamic Bubble Array, AIP Conference Proc., No. 10, Part I, 1972, Amer. Inst. of Phys., N.Y., 1973, pp. 403–407.
Akselrad, A. Detection of Mag. Imperfections, AIP Conf. Proc., No. 10, Part I, 1972, Amer. Inst. of Phys. N.Y., 1973, pp. 408–412.

Primary Examiner—Robert J. Corcoran
Attorney, Agent, or Firm—Frank R. Trifari; Carl P. Steinhauser

[57] ABSTRACT

A device for testing magnetic thin layers for defects, in particular "bubble" films in which a magnetic medium in which a recurring pattern of elongate areas magnetized alternately in opposite senses is recorded is moved relative to the layer while the layer is opposite the magnetic medium so that a corresponding pattern of mutually parallel strip-shaped "bubble" domains is formed in the film. Deviations in said pattern are an indication of defects in the film.

9 Claims, 2 Drawing Figures

APPARATUS FOR TESTING THIN LAYERS OF BUBBLE DOMAIN MATERIAL FOR DEFECTS

The invention relates to a device for testing magnetic thin layers for magnetically active defects and comprising a magnetic device to generate magnetic domains in a layer to be tested, and an optical device to visualize the magnetic domains via a magneto-optical effect.

Such a device is known from "IBM Technical Disclosure Bulletin", Vol. 15, No. 11, April, 1973, pp. 3582–83.

In the manufacture of in particular magnetic "bubble" domain materials, for example, monocrystalline or amorphous garnet films (see, for example, "IEEE Transactions on magnetics", September, 1971, pp. 404–409), it is important to have a means to inspect the magnetic quality of the films in a stage in which no "overlay" structures are provided yet. Magnetically active defects can actually attract or repel magnetic bubble domains and, depending on the bubble domain-to-defect interaction, such a defect occurring in a bubble domain film may render the same unfit for use in a given bubble domain device.

The prior art device comprises a glass plate on which an array of mutually parallel current carrying wires is provided which are interconnected per pair. A film to be tested is arranged at a small distance herefrom and such a current is conveyed through the wires that a number of bubble domains with regular ordering is produced in the film (so-called bubble lattice). Said bubble lattice is made to oscillate, for example, with an alternating current. A photograph made via a polarisation microscope then shows a vague image in the sites where no defects occur but in the sites where defects do occur the bubbles remain hanging, as it were, and the photograph will show a sharp image there. A series of photographs with increasing current strengths present the possibility of distinguishing which defects are weak and which are strong (quantitative gradation).

The known device exhibits the following drawbacks:

A part of a film to be tested is present below the current wires so that movement and making a second photograph for the complete inspection of the film are necessary.

The magnetic fields around the wires are not readily concentrated so that the produced bubble lattice shows a rather coarse structure so that very small defects cannot be visualized. In addition, the wires of the wire array cannot be provided unrestrictedly closely together, which also involves a certain coarseness of the bubble lattice.

Furthermore the construction of the device with current wires restricts the choice of lattices to be used.

It is the object of the invention to provide a device which does not exhibit the said drawbacks.

For that purpose, the device according to the invention is characterized in that the magnetic device comprises a magnetic medium in which a pattern having a given periodicity of elongate areas, magnetized alternately in opposite directions is longitudinally recorded, the pattern having such a field strength that, when the magnetic medium and the layer to be tested are placed at a small distance from each other, a pattern having a corresponding periodicity of mutually parallel domains and groups of domains, respectively, is produced in the layer.

The advantages hereof are the following:

Since a magnetic pattern on a magnetic medium is used (for example, a magnetic tape) a structure for generating the domains can be realized which is much finer than that of the pattern of wires used in the known device.

The magnetic fields on a magnetic tape are much better concentrated than the fields around a current wire so that for this reason also a much finer structure is possible.

The magnetic pattern can be recorded on a magnetic tape in a conventional manner by means of, for example, a magnetic head so that a large variation in the patterns can be realized in an easy manner.

As will be described hereinafter, an additional advantage is that the defect detection is not based on differences in definition of a visualized domain pattern but on deviations from a geometric pattern.

In this connection a preferred embodiment of the device according to the invention is characterized in that the field strength of the magnetic pattern and the distance between the magnetic medium and the layer to be tested are such that a pattern of a strip-shaped domains is generated in the layer.

When defects are not clearly visible it may present advantages to displace the layer to be tested over a small distance with respect to the magnetic device. A defect in the layer will retain the existing magnetisation pattern, while the strip-shaped domains bend out around the defects so as to adapt to the newly prescribed pattern. As a result of this the defect becomes readily visible. Therefore a further embodiment of the device according to the invention is characterized in that means are present to move the magnetisable medium and a layer to be tested relative to each other so as to make the defects more clearly visible.

The device according to the invention also presents a simple possibility of quantitative gradation of the defects. For that purpose, the field strength prescribed by the magnetic device should vary stepwise.

For that purpose, a first preferred embodiment of the device according to the invention is characterized in that for the quantitative gradation of occurring defects, the field strength of the magnetized regions increases or decreases stepwise along the magnetic medium.

For that purpose a second preferred embodiment of the device according to the invention is characterized in that for the quantitative gradation of occurring defects a non-magnetic layer of step-like varying thickness is provided on the magnetic medium, the width of the steps permitting the arrangement of a layer to be tested.

Within the scope of the invention it may present advantages in visualizing defects, as will be described hereinafter, to generate a magnetic auxiliary field at the area of a layer to be tested.

For that purpose, a further preferred embodiment of the device is characterized in that means are provided to produce a magnetic auxiliary field at the area of a layer to be tested.

The invention will be described in greater detail, by way of example, with reference to the drawing.

Figure 1:
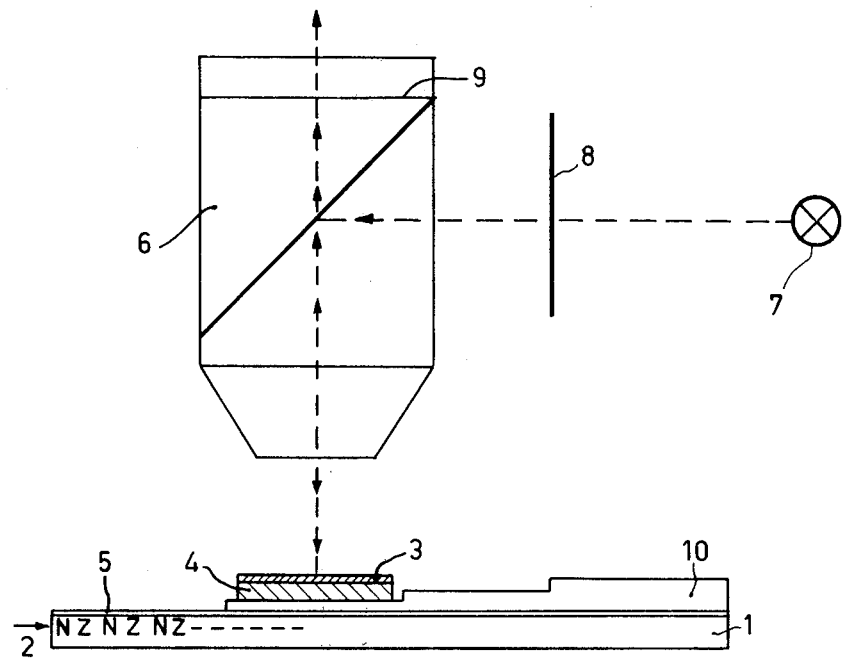
FIG. 1 shows diagrammatically a device for visualising defects in magnetic thin layers.

FIG. 1 shows a bubble layer 4 grown epitaxially on the non-magnetic substrate 3. A periodical magnetic pattern 2 is written in the coatings of the magnetic tape 1 (which may also be any other type of magnetic recording medium), for example by means of a magnetic head, which pattern has a wavelength which is between one and 4 times the stable strip width in the absence of an external field of the strip domains present in the layer 3. The pattern 2 consists of very elongate areas, for example, 10 microns wide and 10,000 microns long, of alternately magnetic north poles and south poles. The written amplitude, the strength of the poles, can easily be made so large that said written, fixed pattern is printed over on the layer 4. Large defects, for example a hole in the layer, interrupt said pattern which can be visualised very readily via the Faraday effect when the tape 1 has a reflecting layer. For visualizing, an incident light polarisation microscope 6 is used together with a light source 7, a polariser 8 and an analyser 9. When the field strength prescribed by the tape 1 is chosen to be smaller, more defects become visible as deviations of the pattern of parallel lines. In order to achieve a gradation of the defects (so a type of calibration) the amplitude of the signal written in the tape 1 may be varied stepwise (for example in steps of 10 dB). Another possibility is to arrange between the tape and the layer 4 to be tested a non-magnetic plate 10, of a transparent material having a reflecting surface and a step-like varying thickness.

The tape 1 itself is rather flexible so that with a good precaution against dust the contact between the layer 4 to be tested and the tape 1 can be very good. For that matter said contact can be checked on interference phenomena between the surface of the tape and the bubble layer.

Figure 2:
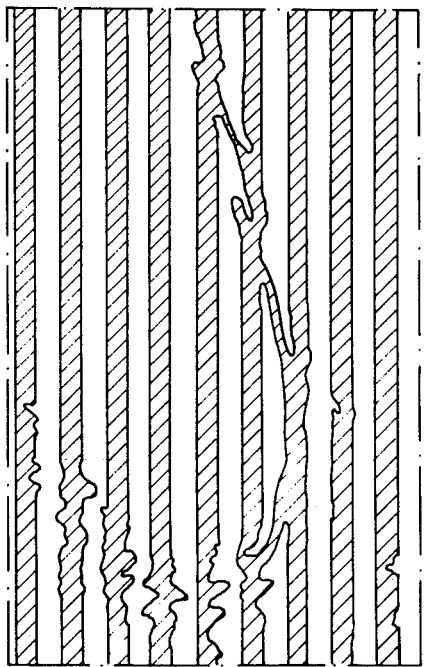
FIG. 2 shows an image of a thin layer observed by means of the device shown in FIG. 1.

FIG. 2 shows an image obtained by means of the device described with reference to FIG. 1, which gives an indication of the magnetic quality of the tested layer. A pattern of parallel lines is clearly visible which is slightly disturbed in the center. The wavelength of the signal written on the tape 1 was in this case 48 microns, the stable strip width of the domains in the tested crystal being approximately 15 microns.

Figure 3:
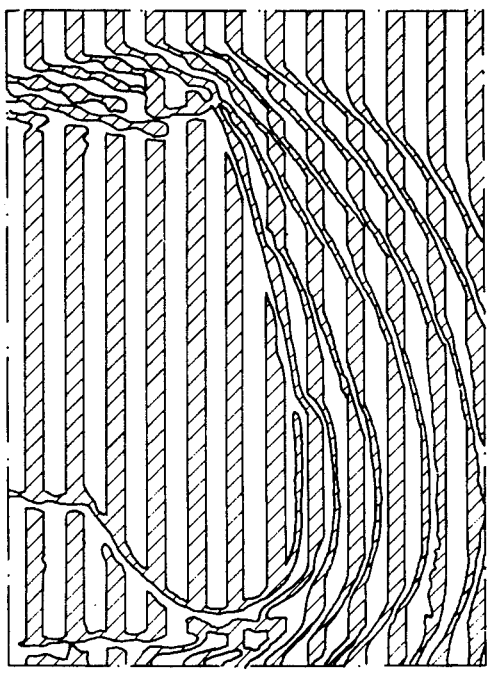
FIG. 3 shows the image which is observed after a slight movement of the thin layer.

FIG. 3 shows an image of the same layer but in this case the layer is slightly moved with respect to the position it occupied in FIG. 1. The defect in the layer is much better visible in this case since it has retained its own pattern upon moving, while the strips are bent out around the defect.

The tape-to-thin layer interaction can be intensified by carrying out the procedure in a comparatively weak alternating field of a few tens of Oersteds, the direction of which is substantially normal to the layer. Small disturbances in the pattern of strips which are due to lower order defects then disappear.

Another possibility is presented by applying a direct field. When a comparatively weak direct field is applied substantially normal to the layer 4 either the black or the white strips are magnetically injured. The injured strips become less stable and are hence more sensitive to disturbances. When a direct field is applied having a direction which is substantially parallel to the layer 4 certain defects such as scratches in the substrate 3, which would otherwise not be visible, become visible. A direct field of a few hundreds of Oersteds should be supplied for that purpose.

What is claimed is:

1. A device for testing thin layers of bubble domain material for magnetically active defects comprising a magnetic medium having a spatially alternating and periodic field recorded thereon for forcing, when brought in facing relationship with a layer to be tested, an array of planar, equally spaced magnetic domains into said layer, means for relative movement between the magnetic medium and the layer to be tested in a direction substantially normal to the magnetic domains, and magneto-optical means for visualizing the magnetic domains.

2. A device as claimed in claim 1 wherein the period of the field configuration is between 1 and 4 times the stable width of the strip-shaped domains in the absence of a magnetic field.

3. A device as claimed in claim 1, wherein the magnetic medium has subsequent areas which present a strength of the field configuration which increases from one area to the other.

4. A device as claimed in claim 1, wherein on the surface of the magnetic medium adjacent the layer to be tested, a non-magnetic platelet having a thickness which increases step-by-step is provided, the width of the steps permitting the arrangement of said layer.

5. A device as claimed in claim 4, wherein the non-magnetic platelet has a reflecting surface.

6. A device as claimed in claim 1, wherein the surface of the magnetic medium adjacent the layer to be tested is reflective.

7. A device as claimed in claim 1, wherein means are provided to produce a magnetic auxiliary field in the layer to be tested.

8. A device as claimed in claim 7, wherein the auxiliary field is an alternating field.

9. A device as claimed in claim 7, wherein the auxiliary field is a direct field.

* * * * *